United States Patent [19]

Atwood

[11] Patent Number: 5,133,868
[45] Date of Patent: Jul. 28, 1992

[54] IDENTIFICATION OF SULFONATION BY-PRODUCTS BY ION CHROMATOGRAPHY

[75] Inventor: Sonia E. Atwood, Littleton, Colo.

[73] Assignee: Marathon Oil Comany, Findlay, Ohio

[21] Appl. No.: 773,383

[22] Filed: Oct. 7, 1991

[51] Int. Cl.$^5$ .............................................. B01D 15/08
[52] U.S. Cl. .................................. 210/656; 210/635; 210/198.2; 436/161; 528/482
[58] Field of Search ................ 55/67, 386; 73/61.1 C; 210/635, 656, 659, 198.2; 436/161, 162; 528/482

[56] References Cited

U.S. PATENT DOCUMENTS

| | | | |
|---|---|---|---|
| 4,217,223 | 8/1980 | Baba | 210/198.2 |
| 4,242,207 | 12/1980 | Ford | 210/500.1 |
| 4,699,718 | 10/1987 | Jones et al. | 210/659 |
| 4,728,344 | 1/1987 | Stacy | 55/67 |
| 4,902,751 | 2/1990 | Lewellyn et al. | 525/340 |
| 4,995,982 | 2/1991 | Barthorpé | 210/634 |

FOREIGN PATENT DOCUMENTS 1495761  2/1970  Fed. Rep. of Germany ... 210/198.2

OTHER PUBLICATIONS

E. Sacher, "The Determination of Trace Inorganic Contaminants in Polyamides", IEEE Transactions on Electrical Insulation, vol. E 1-18, No. 4, pp. 369-373, 1983.

O'Dell et al., "Determination of Inorganic Anions in Water by Ion Chromatography-Method 300.0", EPA-600/4-84-017, Mar. 1984, pp. 300.0-1 to 300.0-5.

Smith-Palmer et al., "The Identification of Alkyl-Sulfates and Sulfonates in Atmospheric Samples by Ion Chromatography", The Science of the Total Environment, 83(1989), pp. 185-190.

L. A. Verkruyse, "Reverse-Phase Ion Pair Chromatography (HPLC) of Alkylbenzene Sulfonates", SPE Paper 11781, 1983 pp. 105-114.

"Installation Instructions and Troubleshooting Guide for the Omnipac PAX-10U Analytical Columns", Dionex Corporation Document No. 034216 Revision OS, Apr. 23, 1989, pp. 1-42.

Primary Examiner—Ernest G. Therkorn
Attorney, Agent, or Firm—Jack L. Hummel; Jack E. Ebel

[57] ABSTRACT

A method for identification and quantification of sulfonation by-products by ion chromatography. The method utilizes 2 eluants and preferably 3 eluants to identify and quantify the by-products on a single chromatographic run.

19 Claims, No Drawings

IDENTIFICATION OF SULFONATION BY-PRODUCTS BY ION CHROMATOGRAPHY

BACKGROUND OF INVENTION

1. Technical Field

This invention relates to the identification of sulfonation by-products in polymeric sulfonate, and more particularly, to the identification of and quantification of such sulfonation by-products by ion chromatography.

2. Description of Related Art

Polymeric sulfonates, such as polyvinyl sulfonates, are effectively utilized to inhibit the formation of scale, particularly inorganic sulfate such as barium sulfate, in subterranean formations. Polymeric sulfonates are conventionally polymerized from commercially available solutions containing a monomer in the presence of a suitable catalyst. For example, polyvinyl sulfonate can be polymerized from a commercially available, dilute, e.g., 25–50 weight percent, aqueous solution of vinylsulfonic acid, sodium salt, in the presence of a suitable catalyst, such as ammonium persulfate or sodium bisulfite. The resultant aqueous polymerization solution contains undesirable by-products of sulfonation, such as sulfate and/or chloride ions and hydroxyethyl sulfonate, and unreacted vinylsulfonic acid sodium salt monomer, in addition to polyvinyl sulfonate. The presence of such undersirable by-products can be extremely deleterious when a polymeric sulfonate is used as a scale inhibitor. Thus, solvents, such as methanol, ethanol and acetone, have been employed to remove undesirable by-products of sulfonation from aqueous polymerization solutions containing polymeric sulfonates. Typical solvent removals are found in German Patent No. 1 495 761 to Hoechst and U.S. Pat. No. 4,995,982 to Barthorpe.

Typical deleterious polymeric sulfonate contaminants are sulfate, chloride, hydroxyethylsulfonate (HES), and sodium vinylsulfonate (SVS). Sulfate ions cannot be identified or quantified by any of the conventional methods, such as size exclusion chromatography, gravimetric turbidimetric precipitation techniques, since compounds, such as ethionic acids, act as sulfate does in such techniques. However, ion chromatography can be used to identify sulfate ion. Ion chromatography is a separation technique which employs a mobile phase, i.e., an eluant, to transport a liquid sample to be analyzed through a stationary phase, i.e., an analytical column. The column has ion exchange groups bound thereto to ionically attract those components in a given liquid sample which have an affinity for the ion exchange groups. However, analysis of polymeric sulfonate samples for contaminants such as sulfate ion by ion chromatography has proved troublesome since the polymeric sulfonate tends to plug the column thereby restricting flow of the sample. Thus, a need exists for a method of analyzing a sample of a polymeric sulfonate by ion chromatography to determine the amount of certain deleterious by-products of sulfonation contained therein.

It is an object of the present invention to provide a method of quantifying the deleterious by-products of sulfonation in a polymeric sulfonate sample by ion chromatography.

It is a further object of the present invention to provide a method of determining the degree by which such deleterious by-products of sulfonation are removed by a given washing process.

It is another object of the present invention to provide a process for simultaneously identifying and quantifying several deleterious by-products of sulfonation present in a partly aqueous solution.

SUMMARY OF INVENTION

To achieve the foregoing and other objects, and in accordance with the purposes of the present invention, as embodied and broadly described herein, the present invention is a method for identifying and quantifying a deleterious by-product of sulfonation present in a polymeric sulfonate comprising the steps of a) diluting a sample of polymeric sulfonate with water, b) injecting said sample into an ion chromatography and c) combining the sample with eluant in the ion chromatograph. The by-product is separated, identified and quantified by the ion chromatograph. In one embodiment of the invention, the eluant is comprised of a first and a second eluant. The first eluant has a sodium hydroxide concentration from about 0.7 mM to about 1.0 mM and a methanol concentration of about 5% to about 7.5% by volume. The second eluant has a sodium hydroxide concentration of about 150 mM to about 200 mM and a methanol concentration of about 5% by volume.

In another embodiment of the invention, the eluant is comprised of a first, a second and a third eluant. The first eluant has a sodium hydroxide concentration of about 0.7 mM and a methanol concentration of about 7.5% by volume. The second eluant has a sodium hydroxide concentration of about 150 mM and a methanol concentration of about 5% by volume. The third eluant has about 90% by volume acetonitrile and about 10% by volume water.

DESCRIPTION OF THE PREFERRED EMBODIMENTS

The present invention is a method to quantify deleterious by-products of sulfonation in an aqueous polymerization solution of a polymeric sulfonate, by ion chromatography and to ensure that such by-products of sulfonation are adequately removed from the polymerization solutions by washing techniques. The method utilizes the flow of eluant mixtures through an ion chromatography column to separate the contaminants found in a polymeric sulfonate polymerization solution. Preferably, the analytical column is a highly crosslinked, microporous core with a particle diameter of 8 $\mu$m. The ethylvinylbenzene/divinylbenzene polymeric core is produced in a manner so that the core has a reactive exterior surface to which a polymeric colloid can be attached. This polymeric colloid, or latex particulate is functionalized with a quaternary ammonium base and contains the actual anion exchange sites. The polymeric core is then coated with the polymeric colloid to create a solvent compatible ion exchange substrate. An exemplary analytical column is sold under the trade name designation OmniPac TM PAX-100 by Dionex Corporation.

Any ion chromatograph which is capable of running samples through analytical columns, such as Dionex's OmniPac PAX-100 can be used to practice this invention. The chromatograph used to develop this technique and used in the later examples is a Dionex 2000i with a gradient pump equipped with polyetherether ketone (PEEK) tubing and fittings, conductivity detector (CDM-II), Eluent Degas Module (EDM-2), autosampler and AI-450 software. Columns used were the Anion Trap Column (ATC), OmniPac PAX-100, PAX-100 Guard, and an Anion Micromembrane ™ Suppressor (AMMS-II) operating via an anion regeneration system. All this equipment is manufactured by Dionex Corporation.

To begin the method, the following steps are taken. First the columns are prepared per the column manufacturer's instructions. Second, inorganic standards are prepared from ultra-dry, 99.99% sodium chloride and 99.999% sodium sulfate. Hydroxyethylsulfonate is prepared from 98% isethionic acid sodium salt, that is freeze-dried. Sodium vinylsulfonate is prepared from vinylsulfonate monomer, sodium salt (30% in water). Standard stock solutions of approximately 1000 $\mu$g inorganic standard per gram of 18 megohm purity water are prepared for each of the four components. A set of mixed standards of chloride and sulfate can be prepared. Individual standards for HES should be prepared fresh as they may contain small amounts impurities and the composition will degrade with time. The individual standard for SVS must also be prepared fresh as it can polymerize over time. Third, eluants are prepared from 50% sodium hydroxide, methanol (suitable for HPLC), acetonitrile (suitable for HPLC) and water having a purity of 18 megohm. All eluants should be degassed with helium and kept under a blanket of helium at all times. Eluant 1 is a sodium hydroxide (NaOH) and methanol (MeOH) mixture having a NaOH concentration of about 0.7 mM to about 1.0 mM and a MeOH concentration of about 5% to about 7.5% by volume. Preferably the first eluant is a 1 mM NaOH and 5% MeOH by volume mixture. Most preferably, the first eluant is a 0.7 mM NaOH and 7.5% by volume MeOH mixture. The second eluant is a NaOH and MeOH mixture having a NaOH concentration of about 150 mM to about 200 mM and a MeOH concentration of about 5% by volume. Preferably, the second eluant is 200 mM NaOH and 5% by volume MeOH mixture, and most preferably, the second eluant is 150 mM NaOH and 5% by volume MeOH. A third eluant need not be used, however, the most preferred method is to utilize a third eluant which is 90% by volume acetonitrile (ACN) and 10% by volume 18 megohm purity water. Fourth, the chromatograph is equilibrated and the consistency of the baseline conductivity is checked. The conductivity should be about 2 microsiemens. Fifth, the gradient operating conditions are set and the standards for chloride, sulfate, HES and SVS are run at concentrations of 1, 10, 50, 100, and 500 $\mu$g of standard per gram of solution in water having a purity of 18 megohm and the results are compared with the appropriate calibration curve from Table 1.

TABLE 1

| TWO ELUANT SYSTEM CALIBRATION CURVE | | | |
|---|---|---|---|
| [Chloride]$\mu$g/g | Peak area | [Sulfate]$\mu$g/g | Peak area |
| 0.00 E + 00 | 0.00 E + 00 | 0.00 E + 00 | 0.00 E + 00 |
| 9.23 E − 01 | 7.72 E + 06 | 9.17 E − 01 | 5.95 E + 06 |
| 9.86 E + 00 | 7.92 E + 07 | 9.59 E + 00 | 5.51 E + 07 |
| 1.92 E + 01 | 1.60 E + 08 | 1.92 E + 01 | 1.18 E + 08 |
| THREE ELUANT SYSTEM CALIBRATION CURVE | | | |
| [HES]$\mu$g/g | PEAK AREA | [SVS]$\mu$g/g | PEAK AREA |
| 0.00 E + 00 | 0.00 E + 00 | 0.00 E + 00 | 0.00 E + 00 |
| 9.70 E − 01 | 1.03 E + 06 | 1.06 E + 00 | 1.09 E + 06 |
| 9.97 E + 00 | 1.43 E + 07 | 1.06 E + 01 | 1.69 E + 07 |
| 5.01 E + 01 | 7.80 E + 07 | 7.58 E + 01 | 1.37 E + 08 |

TABLE 1-continued

| | | | |
|---|---|---|---|
| 9.68 E + 01 | 1.62 E + 08 | 1.28 E + 02 | 2.39 E + 08 |
| 4.79 E + 02 | 8.96 E − 08 | 5.70 E + 02 | 1.17 E + 09 |
| [Chloride]$\mu$g/g | PEAK AREA | [Sulfate]$\mu$g/g | PEAK AREA |
| 0.00 E + 00 | 0.00 E + 00 | 0.00 E + 00 | 0.00 E + 00 |
| 9.47 E − 01 | 6.13 E + 06 | 9.92 E − 01 | 4.16 E + 06 |
| 1.01 E + 01 | 7.61 E + 07 | 1.00 E + 01 | 4.42 E + 07 |
| 4.86 E + 01 | 4.18 E + 08 | 4.82 E + 01 | 2.38 E + 08 |
| 1.00 E + 02 | 8.81 E + 08 | 1.00 E + 02 | 5.20 E + 08 |
| 5.01 E + 02 | 4.66 E + 09 | 5.02 E + 02 | 2.80 E + 09 |

Sixth, the sulfonated polymeric sample is then diluted with water, to the desired dilution factor (e.g., a dilution factor of 978.02 is obtained by mixing 1 part of polymeric sample by weight with 978.02 parts by weight of solution with water) then injected, and run on the chromatograph. As will be obvious to one skilled in the art, the desired dilution will depend on the amount of sulfonation by-product present. A suggested starting dilution is 1 part by weight polymeric sulfonate sample to 199 parts by weight water having 18 megohm purity. The desired dilution factor will result in a sulfonation by-product concentration range of 0–500 $\mu$g/g, preferably 0–100 $\mu$g/g and most preferably 0–50 $\mu$g/g. The samples are run for 30 minutes or less, preferably 27 or less minutes and most preferably 24 minutes or less.

The above method is then repeated with varying concentrations of sample until the desired chromatograph peak areas are achieved to adequately identify the amount of chloride, sulfate, HES and SVS present in the sample.

The following examples describe several embodiments of the present invention and set forth the best mode contemplated by the inventors of carrying out the invention. These examples are not to be construed as limiting the scope of the invention thereof.

EXAMPLE 1

Example 1 runs are conducted under the conditions shown in Table 2. All samples are polysulfonate, scale inhibitors of varying polyvinylsulfonate concentration.

TABLE 2

Gradient Ion Chromatograph Operating Conditions
Eluant 1: 1 mM Sodium Hydroxide 5% by Volume Methanol
Eluant 2: 200 mM Sodium Hydroxide 5% by Volume Methanol
Gradient Program:

| Time | Flow Rate (mL/min) | % Eluant 1 | % Eluant 2 | Comment |
|---|---|---|---|---|
| 0.0 | 1.0 | 100 | 0 | Equilibrate |
| 5.1 | 1.0 | 100 | 0 | Load Sample Loop |
| 6.0 | 1.0 | 100 | 0 | Inject Sample |
| 8.6 | 1.0 | 100 | 0 | Turn Inject Valve Off |
| 22.0 | 1.0 | 70 | 30 | 15 Minute Ramp |

Columns: Anion Trap Column, OmniPac PAX-100 and PAX 100 Guard
Suppressor: Anion Micromembrane Suppressor-II (AMMS-II)
Automatic Regeneration: 50 mN Sulfuric Acid, Flow Rate = 15 ml/min
Injection: 5 $\mu$L
Detection: Conductivity

TABLE 3

| Run | Sample | Dilution Factor | Run Time (minutes) | Concentration ($\mu$g/g) | Area |
|---|---|---|---|---|---|
| ION: Chloride | | | | | |
| 1 | I | 978.02 | 10.58 | 3045.6 | 25246020 |
| 2 | M | 417.04 | 10.19 | 1243.8 | 24192358 |
| 3 | N | 417.98 | 0 | 0 | 0 |
| 4 | O | 585.56 | 10.15 | 6559.8 | 90830945 |
| 5 | P | 413.78 | 10.53 | 9691.7 | 196517000 |
| ION: Sulfate | | | | | |

TABLE 3-continued

| Run | Sample | Dilution Factor | Run Time (minutes) | Concentration (μg/g) | Area |
|---|---|---|---|---|---|
| 1 | I | 978.02 | 13.62 | 12988.9 | 79251400 |
| 2 | M | 417.04 | 13.54 | 7919.936 | 116629880 |
| 3 | N | 417.98 | 13.55 | 7351.9 | 107454460 |
| 4 | O | 417.98 | 13.56 | 5095.6 | 50063800 |
| 5 | P | 413.78 | 13.62 | 6905.3 | 101557900 |

Example 1 shows that sulfate ion and chloride ion can be both identified and quantified in samples of polymeric sulfonates.

EXAMPLE 2

Example 2 runs are conducted under the conditions shown in Table 4. All samples are polysulfonate scale inhibitors of varying polyvinylsulfonate concentration. Sample A is an untreated scale inhibitor. Sample B is the same scale inhibitor as on Sample A that has been washed with a 25% by volume methanol solution (MeOH) and Sample C is the same scale inhibitor as in Sample A that has been washed with a 40% by volume methanol solution.

TABLE 4

GRADIENT ION CHROMATOGRAPH OPERATING CONDITIONS

Eluant 1: 0.7 mM Sodium Hydroxide 7.5% by volume Methanol
Eluant 2: 150 mM Sodium Hydroxide 5% by volume Methanol
Eluant 3: 90% by volume Acetonitrile 10% by volume Water Gradient Program:

| Time (Min) | Flow Rate (mL/min) | % Eluant 1 | % Eluant 2 | % Eluant 3 | Comment |
|---|---|---|---|---|---|
| 0.0 | 1.0 | 100 | 0 | 0 | Equilibrate |
| 5.1 | 1.0 | 100 | 0 | 0 | Load |
| 6.0 | 1.0 | 100 | 0 | 0 | Inject |
| 23.0 | 1.0 | 50 | 20 | 30 | Ramp 1 |
| 30.0 | 1.0 | 209 | 40 | 40 | Ramp 2 |

Columns: Anion Trap Column, OmniPac PAX-100 and PAX 100 Guard
Suppressor: Anion Micromembrane Suppressor-II (AMMS-II)
Auto Regen: 100 mN Sulfuric Acid, Flow Rate: 11.0–11.5 ml/min
Injection: 5 μL
Detection: Conductivity

TABLE 5

ION: Hydroxyethylsulfonate

| Run | Sample | Dilution Factor | Run Time (minutes) | Concentration (μg/g) | H Area |
|---|---|---|---|---|---|
| 1 | A Untreated | 208.19 | 6.75 | 28150.8 | 2.36 E + 08 |
| 2 | B 25% MEOH | 39.617 | 6.58 | 6218.25 | 2.77 E + 08 |
| 3 | C 40% MEOH | 42.244 | 6.66 | 4122.33 | 1.63 E + 08 |
| 4 | D | 434.41 | 6.54 | 20314.5 | 72697000 |
| 5 | E | 394.47 | 6.7 | 15300.6 | 60039000 |
| 6 | F | 264.78 | 6.54 | 16157.5 | 97634600 |
| 7 | G | 117.77 | 6.61 | 17154.8 | 2.56 E + 08 |
| 8 | H | 120.18 | 6.4 | 18019.7 | 2.64 E + 08 |
| 9 | I | 126.64 | 6.08 | 10245.9 | 1.33 E + 08 |
| 10 | J | 120.55 | 6.64 | 11706.6 | 1.63 E + 08 |
| 11 | K | 185.3 | 6.45 | 19462.9 | 1.78 E + 08 |
| 12 | L | 204.82 | 6.03 | 31784.2 | 2.74 E + 08 |

ION: SVS

| Run | Sample | Dilution Factor | Run Time (minutes) | Concentration (μg/g) | S Area |
|---|---|---|---|---|---|
| 1 | A Untreated | 208.19 | 7.5 | 7615.02 | 64756800 |
| 2 | B 25% MEOH | 39.617 | 7.35 | 1153.56 | 51001663 |
| 3 | C 40% MEOH | 42.244 | 7.41 | 541.13 | 20929000 |
| 4 | D | 434.41 | 7.31 | 188.907 | 447200 |
| 5 | E | 394.47 | 7.42 | 3470.48 | 13878800 |
| 6 | F | 264.78 | 0 | 0 | 0 |
| 7 | G | 117.77 | 0 | 0 | 0 |
| 8 | H | 120.18 | 0 | 0 | 0 |
| 9 | I | 126.64 | 0 | 0 | 0 |
| 10 | J | 120.55 | 7.38 | 113.988 | 972400 |
| 11 | K | 185.3 | 0 | 0 | 0 |
| 12 | L | 204.82 | 6.81 | 2933.85 | 23721600 |

ION: Chloride

| Run | Sample | Dilution Factor | Run Time (minutes) | Concentration (μg/g) | C Area |
|---|---|---|---|---|---|
| 1 | A Untreated | 208.19 | 8.48 | 56.6439 | 1762000 |
| 2 | B 25% MEOH | 39.617 | 8.33 | 13.0277 | 2129600 |
| 3 | C 40% MEOH | 42.244 | 8.37 | 4.28957 | 657600 |
| 4 | D | 434.41 | 8.12 | 6903.23 | 1.28 E + 08 |
| 5 | E | 394.47 | 8.34 | 163.353 | 2681800 |
| 6 | F | 264.78 | 8.21 | 178.867 | 4374800 |
| 7 | G | 117.77 | 8.29 | 178.952 | 10528800 |
| 8 | H | 120.18 | 8.11 | 187.991 | 10872400 |
| 9 | I | 126.64 | 7.66 | 3428.01 | 2.27 E + 08 |
| 10 | J | 120.55 | 8.14 | 2056.58 | 1.38 E + 08 |
| 11 | K | 185.3 | 7.97 | 5368.57 | 2.44 E + 08 |
| 12 | L | 204.82 | 7.62 | 5900.87 | 2.42 E + 08 |

ION: Sulfate

| Run | Sample | Dilution Factor | Run Time (minutes) | Concentration (μg/g) | S Area |
|---|---|---|---|---|---|
| 1 | A Untreated | 208.19 | 14.66 | 6026.48 | 140123400 |
| 2 | B 25% MEOH | 39.617 | 14.47 | 2771.58 | 356366800 |
| 3 | C 40% MEOH | 42.244 | 14.42 | 2918.47 | 351610000 |
| 4 | D | 434.41 | 14.55 | 5543.4 | 57932400 |

TABLE 5-continued

| | | | | | |
|---|---|---|---|---|---|
| 5 | E | 394.47 | 14.52 | 6616.52 | 78306800 |
| 6 | F | 264.78 | 14.51 | 3139.33 | 53340000 |
| 7 | G | 117.77 | 14.38 | 4716.01 | 196473200 |
| 8 | H | 120.18 | 14.36 | 2892.44 | 115346200 |
| 9 | I | 126.64 | 14.05 | 14745.5 | 613264789 |
| 10 | J | 120.55 | 14.27 | 3499 | 140520663 |
| 11 | K | 185.3 | 14.22 | 5621.45 | 147181547 |
| 12 | L | 204.82 | 14.15 | 6678.25 | 158700200 |

Example 2 shows the advantage of a 3 eluant method over a 2 eluant method. Although HES and SVS can be identified in a 2 eluant system, the 3 eluant method enables HES and SVS to be identified with improved overall peak resolution. Example 2 also shows that a simultaneous identification of sulfate, SVS, HES and chloride can be conducted in a single ion chromatography run and that the extent of removal of by-products by a given solvent wash technique can be quantified, and therefore, the efficiency of the solvent wash technique can be calculated. Additionally, a 3 eluant system reduces the necessity of frequent guard column changing and eases cleaning of the main chromatograph column.

It should be noted that several peaks on the chromatograph using a 3 eluant system have yet to be identified. However, it is suspected that some peaks are the sulfate ester of 2-hydroxyethansulfonic acid (ethionic acid) and oligomers of HES. Therefore this method may permit identification of other sulfonation by-products which are not specified herein.

Throughout the description, the process of the present invention has been characterized as suitable for a polymeric sulfonate, such as a polyvinyl sulfonate. As will be evident to those skilled in the art, the process of the present invention is equally applicable to copolymers of polyvinyl sulfonates as well as other polymeric sulfonates, such as polystyrene sulfonate and copolymers thereof and 2-acrylamide, 2-methylpropane sulfonic acid and copolymers thereof. The process can also be used to analyze monomer, polymer and brine solutions.

While the preferred embodiments have been fully described and depicted for the principles of the present invention, it will be appreciated by those skilled in the art that modifications and changes may be made thereto without departing from the scope of the invention set forth in the appended claims.

I claim:

1. A method for identifying and quantifying a deleterious by-product of sulfonation present in a polymeric sulfonate comprising:
   a) diluting a sample of polymeric sulfonate with water;
   b) injecting said sample into an ion chromatograph; and
   c) combining said sample with eluant in said ion chromatograph, said by-product being separated, identified and quantified by said ion chromatograph.

2. The method of claim 1 wherein said polymeric sulfonate is diluted to 199 parts water to every 1 part sulfonate by weight.

3. The method of claim 1 wherein said eluant is comprised of a first eluant and a second eluant.

4. The method of claim 3 wherein said first eluant is comprised of a sodium hydroxide and methanol mixture and said second eluant is comprised of a sodium hydroxide and methanol mixture.

5. The method of claim 4 wherein sodium hydroxide concentration is about 0.7 mM to about 1.0 mM, and said methanol concentration is about 5% to about 7.5% by volume in said first eluant and wherein said sodium hydroxide concentration is about 150 mM to about 200 mM and said methanol concentration is about 5% by volume in said second eluant.

6. The method of claim 5 wherein said sodium hydroxide concentration is about 1 mM and said methanol concentration is about 5% by volume in said first eluant and said sodium hydroxide concentration is about 200 mM and said methanol concentration is about 5% by volume in said second eluant.

7. The method of claim 1 wherein said eluant is comprised of a first eluant, a second eluant and a third eluant, said first eluant comprising a sodium hydroxide and methanol mixture, said second eluant comprising a sodium hydroxide and methanol mixture and said third eluant comprising an acetonitrile and water mixture.

8. The method of claim 7 wherein said sodium hydroxide concentration is about 0.7 mM to about 1.0 mM and said methanol concentration is about 5% to about 7.5% by volume in said first eluant, and said sodium hydroxide concentration is about 150 mM to about 200 mM and said methanol concentration is about 5% by volume in said second eluant.

9. The method of claim 8 wherein said sodium hydroxide concentration is 0.7 mM and said methanol concentration is 7.5% by volume in said first eluant, said sodium hydroxide concentration is 150 mM and said methanol concentration is 5% by volume in said second eluant, and said acetonitrile concentration is 90% by volume and said water concentration is 10% by volume in said third eluant.

10. The method of claim 1 wherein said separation is conducted for less than about 30 minutes.

11. The method of claim 10 wherein said separation is conducted for less than about 27 minutes.

12. The method of claim 11 wherein said separation is conducted for less than about 24 minutes.

13. The method of claim 1 wherein at least two separate by-products of sulfonation are separated, identified and quantified.

14. The method of claim 13 wherein said at least two by-products are simultaneously identified and quantified.

15. A method for determining the degree by which deleterious by-products of sulfonation are removed by a given washing process comprising:
   a) diluting a first sample of unwashed polymeric sulfonate with water;
   b) injecting said sample into an ion chromatograph;
   c) combining said sample with eluant in said ion chromatograph, said by by-product being separated, identified and quantified by said ion chromatograph;
   d) washing a second sample of said unwashed polymeric sulfonate with a solvent;

e) diluting said washed sample with water;

f) injecting said washed sample into said ion chromatograph;

g) combining said washed sample with eluant in said ion chromatograph, said by-product being separated, identified and quantified by said ion chromatograph; and h) comparing the quantity of said by-product identified and separated by step c with the quantity of said by-product identified and separated by step g to determine the degree of by-product removal obtained by washing step d.

16. The method of claim 15 wherein said eluant is comprised of a first eluant and a second eluant, said first eluant comprising a sodium hydroxide and methanol mixture and said second eluant comprising a sodium hydroxide and methanol mixture.

17. The method of claim 16 wherein said sodium hydroxide concentration is about 0.7 mM to about 1.0 mM and said methanol concentration is about 5% to about 7.5% by volume in said first eluant, and said sodium hydroxide concentration is about 150 mM to about 200 mM and said methanol concentration is about 5% by volume in said second eluant.

18. The method of claim 15 wherein said eluant is comprised of a first eluant, a second eluant and a third eluant, said first eluant comprising a sodium hydroxide and methanol mixture, said second eluant is comprising a sodium hydroxide and methanol mixture and said third eluant is comprising an acetonitrile and water mixture.

19. The method of claim 18 wherein said sodium hydroxide concentration is about 0.7 mM to about 1.0 mM and said methanol concentration is about 5% to about 7.5% by volume in said first eluant, said sodium hydroxide concentration is about 150 mM to about 200 mM and said methanol concentration is 5% by volume in said second eluant and said acetronitrile concentration is 90% by volume and said water concentration is 10% by volume in said third eluant.

* * * * *